United States Patent [19]

Didier

[11] Patent Number: 4,913,282

[45] Date of Patent: Apr. 3, 1990

[54] KIT FOR THE HYGIENE OF REMOVABLE DENTAL PROSTHESES

[76] Inventor: Richard Didier, "Fort Charles", 1, rue des Glacis, L-1628 Luxembourg, Luxembourg

[21] Appl. No.: 322,442

[22] Filed: Mar. 13, 1989

[30] Foreign Application Priority Data

Oct. 14, 1988 [FR] France ................................. 88 13598

[51] Int. Cl.⁴ .............................................. A61C 19/10
[52] U.S. Cl. ...................................... 206/83; 206/204; 206/205; 206/207; 206/223; 206/581; 15/167.1
[58] Field of Search ............... 206/15.2, 83, 204, 205, 206/207, 223, 229, 570, 581; 215/1 C; 220/82 R; 15/167.1, 250.28

[56] References Cited

U.S. PATENT DOCUMENTS

| | | | |
|---|---|---|---|
| 390,089 | 9/1888 | McClelland | 206/581 |
| 2,541,595 | 2/1951 | Marshall et al. | 206/83 |
| 2,565,899 | 8/1951 | Wilcox | 206/83 |
| 2,617,519 | 11/1952 | O'Sullivan | 205/205 |
| 2,973,767 | 3/1961 | Cohen | 206/83 |
| 3,603,452 | 9/1971 | Singer | 206/45.16 |
| 3,732,973 | 5/1973 | Crawford | 15/167.1 |
| 3,826,358 | 7/1974 | Butler | 206/204 |
| 4,213,536 | 7/1980 | Hafner | 220/82 R |
| 4,238,604 | 5/1982 | Adams | 15/167.1 |
| 4,625,357 | 12/1986 | De Martino | 15/167.1 |
| 4,689,014 | 8/1987 | Krasner | 206/83 |
| 4,724,570 | 2/1988 | Hitzman | 15/167.1 |
| 4,763,375 | 8/1988 | Vieten | 15/167.1 |
| 4,802,853 | 2/1989 | Krasner | 206/83 |
| 4,816,273 | 3/1989 | Smith et al. | 215/1 C |

*Primary Examiner*—David T. Fidei
*Attorney, Agent, or Firm*—Fishman, Dionne & Cantor

[57] ABSTRACT

A kit, for the hygiene of removable dental prostheses is presented comprising a container with hermetic sealing which can contain at least one prosthesis and is provided with a removable false bottom in order to support the prosthesis above the level of a solution of sterilizing liquid. A porous lining covers the majority of the inner surface of the container and the false bottom.

13 Claims, 5 Drawing Sheets

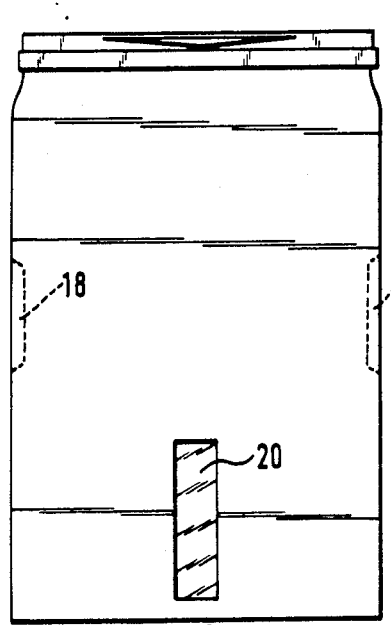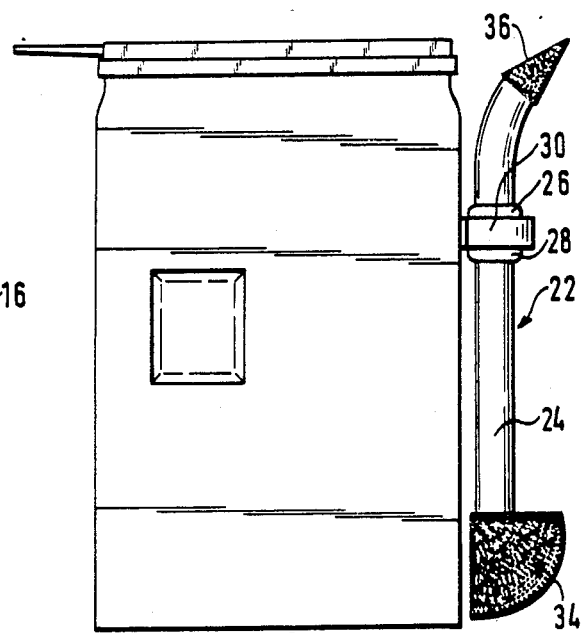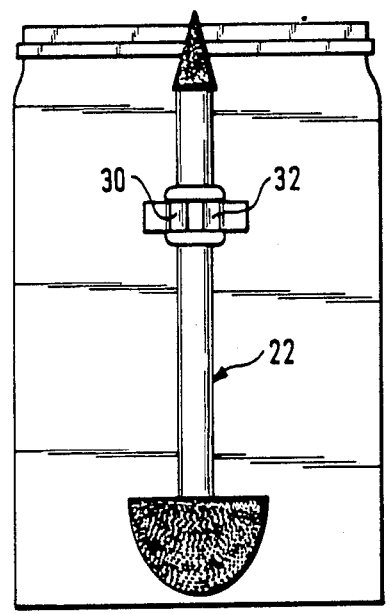
Fig. 2    Fig. 3
Fig. 4

KIT FOR THE HYGIENE OF REMOVABLE DENTAL PROSTHESES

BACKGROUND OF THE INVENTION

The present invention relates to a kit for the hygiene of removable dental prostheses, which consist partially or completely of resin, stellite or other suitable synthetic material.

For many years there has been a great contrast between on the one hand, the exactitude and precision in the shaping of an adjunct prosthesis as well as the multitude of techniques deployed for their production, and, on the other hand, the relatively small number of techniques and materials concerned with the cleaning, sterilization, storage, and transport of such prosthesis.

With regard to cleaning the prosthesis, it is well known that only good regular brushing permits proper cleaning of an adjunct prostheses. Unfortunately, suitable brushes which permit a cleaning which is both easy and effective are lacking. As a result, most patients will be content using conventional toothbrushes and toothpaste for this purpose. However, these brushes do not permit a correct cleaning of the parts to which access is difficult. Also, the use of toothpaste risks concealing the small areas to be cleaned, because of the development of foam.

With regard to the sterilization of the prostheses, this is indispensable in the same way as the brushing. Any prosthesis, of which a part or a whole is made of acrylic resin, is colonized with microorganisms which lodge in the many pores of this material. This is especially true when the prosthesis ages. Regular brushing can remove some of these microorganisms, especially at the surface, but it cannot eliminate them completely, especially in the pores. Yet the elimination of these bacteria is indispensable in order to prevent their accumulation and the formation of tartar and subprosthetic macerations.

Specialists generally recommend that this sterilization be carried out either in a 0.02% chlorhexidine solution or in contact with chlorhexidine vapor. This sterilization also requires appropriate containers, which do not exist at the present time.

Another important problem, and one closely related to sterilization, is the storage of the dental prostheses. Protheses, especially those of acrylic resin, must be kept in a moist medium in order to prevent deformations due to phenomenon of dehydration at the level of the resins. Thus, for the periods during which they are not worn, the prostheses must be stored in a moist medium. If this period is relatively short, for example overnight, the patients who remove their prostheses for the night can immerse them in a sterilizing liquid. However, in case of longer storage periods, complete immersion in a sterilizing liquid is harmful because of the absorption phenomena of the liquid at the level of the resins. This phenomena can result in volumetric variations and reduce the mechanical strength of the prostheses. The long immersion problem can be very common since many patients have prosthesis spares so they are not caught unprepared in the event of a repair or alteration requiring the original prosthesis to be sent to the laboratory.

The transport of removable prostheses, when not worn in the mouth, can also cause problems, since the fragility of these prostheses necessitates a great deal of care in their handling and their storage.

SUMMARY OF THE INVENTION

The above discussed and other problems and deficiencies of the prior art are overcome or alleviated by the dental prostheses kit of the present invention. The dental prostheses kit provides for the complete hygiene of dental prostheses. It facilitates the different operations of brushing, sterilization, overnight and long-term storage, transport, etc. of the removable prostheses.

In accordance with the present invention, the kit for the hygiene of dental prostheses comprises a container with hermetic sealing which can contain at least one prosthesis. The container is provided with a removable false bottom in order to hold the prosthesis above the level of a solution of sterilizing liquid. It also has a porous lining covering the majority of the inner surface of the container and the false bottom.

The false bottom prevents the prosthesis from directly contacting the solution of sterilizing liquid. However, the prosthesis is supported in a damp atmosphere saturated with liquid vapors by virtue of the presence of the porous lining. The prosthesis is therefore in a medium which is ideal for its long-term storage. For a more rapid sterilization or a short-term storage, it is possible to remove the bottom of the container and to immerse the prosthesis directly in the solution of sterilizing liquid.

The container preferably has the form of an upright parallelepiped with a square or rectangular cross-section. The removable bottom rests on four blocks provided in each of the lower corners of the container.

To this end, the four corners of the removable bottom can be configured as square projections relative to the adjacent sides, in order to bear on these corner blocks.

In accordance with a preferred embodiment of the present invention, the container can be divided into two adjacent compartments by means of a removable middle partition, comprising on its two surfaces a porous lining. This permits the storage of two prostheses in the same vessel, for example the prosthesis, which is removed overnight, alongside the spare, or else the auxillary prosthesis and mandibular prosthesis without any risk of the two prostheses interlocking.

This middle partition will advantageously be connected in a detachable manner to the removable bottom in order to form a sort of removable basket. This permits simple removal of the prosthesis or prostheses from the container.

The removable bottom preferably comprises, on each side of the middle partition and on the lower side, a foot consisting of a strip folded in the form of a "V". This forms together with the removable bottom, a triangular structure. Each foot is also provided with a porous lining.

The triangular forms of the two feet can be asymmetrical so as to present in combination, viewed perpendicular to the middle partition, the form of a "W". This allows the basket, when removed from the container, to be placed on a support with a minimum of contact with the container.

The kit of the present invention can also comprise a brush for cleaning prostheses. The brush consists of a rectilinear sleeve, one of the ends of which terminates in a brush of conical shape, while the opposite end terminates in a brush having the shape of a semi-paraboloid. The end consisting of the conical brush is preferably inclined relative to the rectilinear sleeve.

The outer wall of the container of the kit of this invention advantageously comprises two flexible tongues for the attachment of the brush. The brush can include, for this purpose, two rims delimiting a section for attachment of the brush between the flexible tongues.

The hermetic sealing of the vessel is preferrably achieved by means of a swing lid comprising a two-stage closure system.

The above-discussed and other features and advantages of the present invention will be apparent to and understood by those skilled in the art from the following detailed description and drawings.

BRIEF DESCRIPTION OF THE DRAWING

Referring now to the drawings, wherein like elements are numbered alike in the several Figures:

FIG. 2 is front elevation view of the kit of FIG. 1;

FIG. 3 is a side elevation view of the kit of FIG. 1;

FIG. 4 is a rear elevation view of the kit of FIG. 1;

DESCRIPTION OF THE PREFERRED EMBODIMENT

Figure 1:
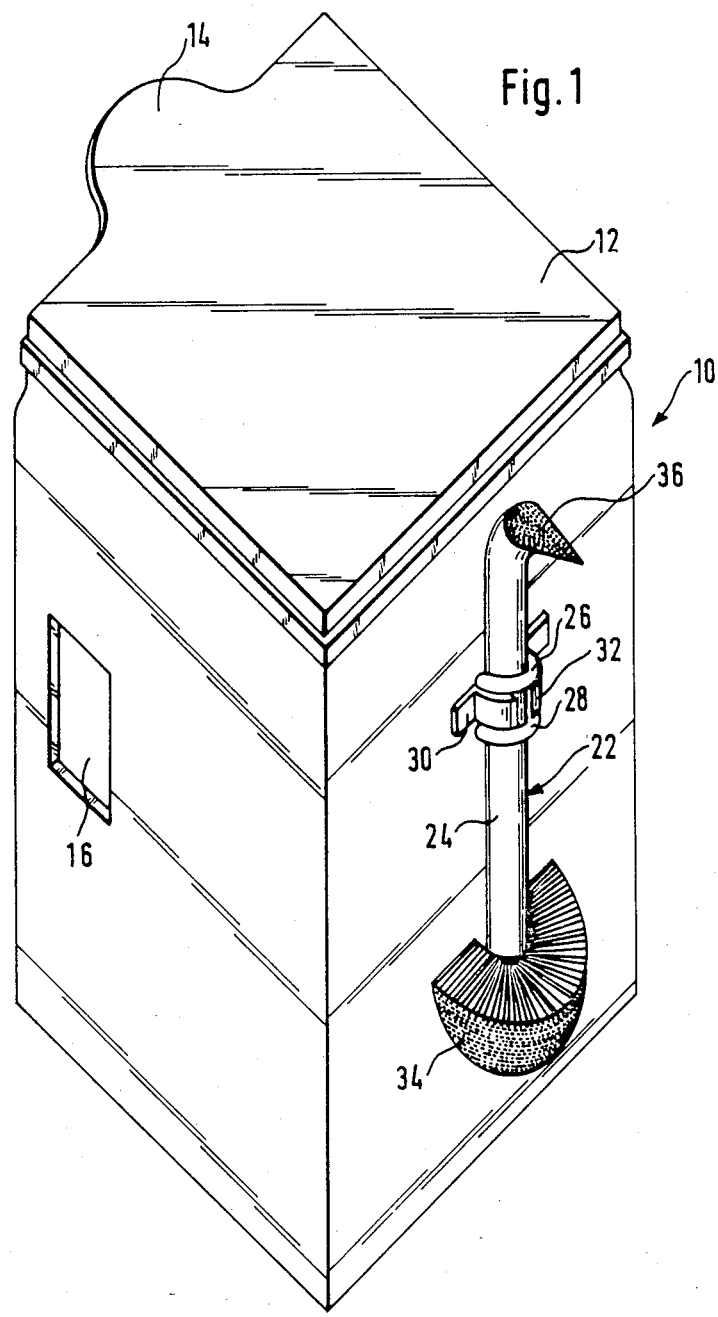
FIG. 1 is a side perspective view of the dental prosthesis kit of the present invention.
Figure 5:
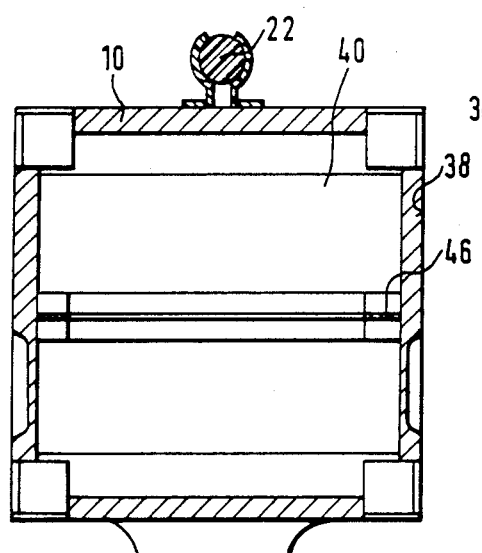
FIG. 5 is a horizontal cross sectional view of the kit of FIG. 1.
Figure 6:
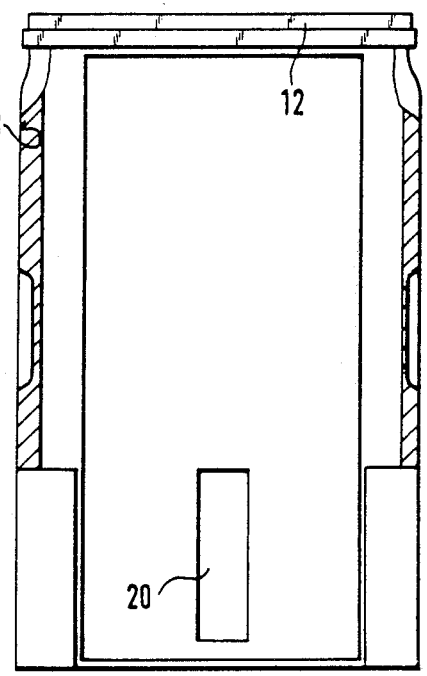
FIG. 6 is a vertical cross sectional view of the kit of FIG. 1.

Referring jointly to FIGS. 1-4, the container for the removable dental prostheses hygiene kit of the present invention is shown generally at 10. Container 10 is suitable for the simultaneous sterilization, short-term and long-term storage and also the transport of removable dental prostheses. In general, container 10 has the overall form of a vertical parallelepiped of square cross-section, provided with an upper swinging lid 12 for ensuring hermetic sealing. Lid 12 preferably includes a tongue 14 for facilitating its operation.

Container 10 preferably comprises, on two opposite faces, depressions 16 and 18 for facilitating its holding between two fingers. A third face of container 10 can comprise a transparent section 20 for checking, from the outside, the level of sterilizing liquid in the inside. In regard to the fourth lateral face of container 10, it can be configured for the attachment of a brush 22 which serves to clean removable prostheses.

This brush 22 consists of a rectilinear handle 24, made for example of synthetic material. Handle 24 is provided with two rims 26 and 28 delimiting, between them, a section by means of which the brush 22 can be attached in an easily detachable manner, between two flexible tongues 30 and 32 provided for this purpose on the fourth lateral face of container 10.

One of the ends of the handle 24 consists of a hard nylon brush 34 taking the form of a semi-paraboloid, as shown in FIGS. 1, 3 and 4. Brush 34 is particularly suitable for the brushing of the extrados, intrados and prosthetic teeth.

The opposite end of handle 24 consists of a brush 36 of conical form, the hairs of which are likewise of hard nylon. Brush 36, which is of the interdental small brush type, is more particularly suitable for brushing the clasps and attachments of the prostheses. In order to improve the maneuverability of the brush, it is preferable for brush 36 to be slightly inclined relative to the longitudinal axis of handle 24 as shown in FIG. 3.

In an alternative embodiment, brush 22 may be attached to container 10 on the face opposite that shown in FIG. 1. This allows brush 22 to be protected by flap 14 of lid 12 and reduces the space required for storing the container.

The inside of container 10 will now be described with reference to FIGS. 5 to 8. The inner surface of container 10 is covered over the greater part, especially its lateral surfaces and lid 12, with a porous lining 38. Lining 38 can consist of a system of fixed compresses of nylon, sponge or cotton. Lining 38 permits the rise of sterilizing solution by means of capillary action along all the inner surfaces of container 10. Sterilizing solution may consist of a 0.02% chlorhexidine solution. The solution is located in the bottom of the container 10. Container 10 thus serves as a container for the sterilizing liquid. The liquid solution evaporates from the surface of the porous lining 38 which ensures a sufficient humidity above the liquid level.

Another function of lining 38 is that of protection. By virtue of its construction and materials, it also functions to dampen impacts during the displacement of container 10.

In order to prevent the prosthesis or prostheses located in container 10 from coming into contact with the solution of sterilizing liquid, a removable bottom 40 is provided. During liquid replenishment, transparent window 20 is provided to ensure that the level does not go beyond removable bottom 40.

In the embodiment shown in FIGS. 5 to 8, there is provided, in the bottom of container 10 in each of the four corners, a block 42. Block 42 supports removable bottom 40. For its part, bottom 40 comprises, at the four corners, square projections 44 projecting beyond the adjacent sides. Bottom 40 rests simply by means of corners 44 on blocks 42. It should be noted that removable bottom 40 comprises the same pourous lining 38 as the inner walls of container 10. This increases the surface available for evaporation.

In another advantageous embodiment of the present invention, a removable vertical middle partition 46 is provided which divides the inside of container 10 into two identical compartments. The advantage of this is that it is possible to store, in the same container, two prostheses at the same time, without the risk of their clasps becoming interlocked.

It is preferable to combine partition 46 with removable bottom 40 in order to form a sort of basket which can be removed from container 10 with the prostheses which it supports. To this end, partition 46 and bottom 40 can comprise complementary slots in order to be fitted in a removable manner into each other and to form the basket-shaped structure shown in FIG. 8. Partition 46 also comprises, in a similar way to the whole of the inside of container 22, a porous lining 38 on each of its faces.

Figure 7:
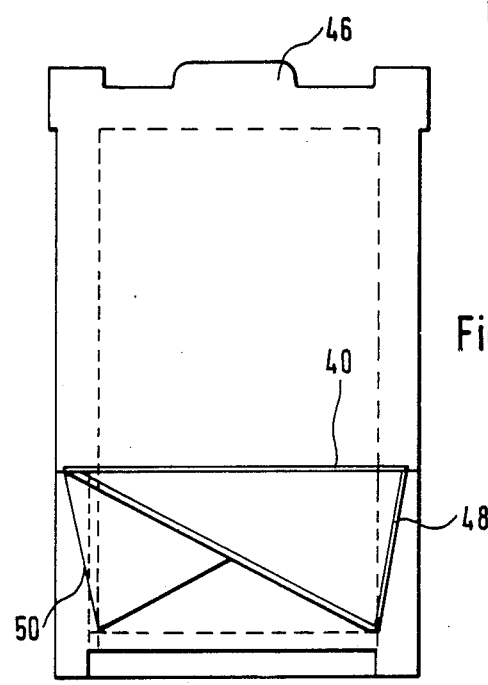
FIG. 7 is a side elevation view of the removable bracket of the kit of FIG. 1.
Figure 8:
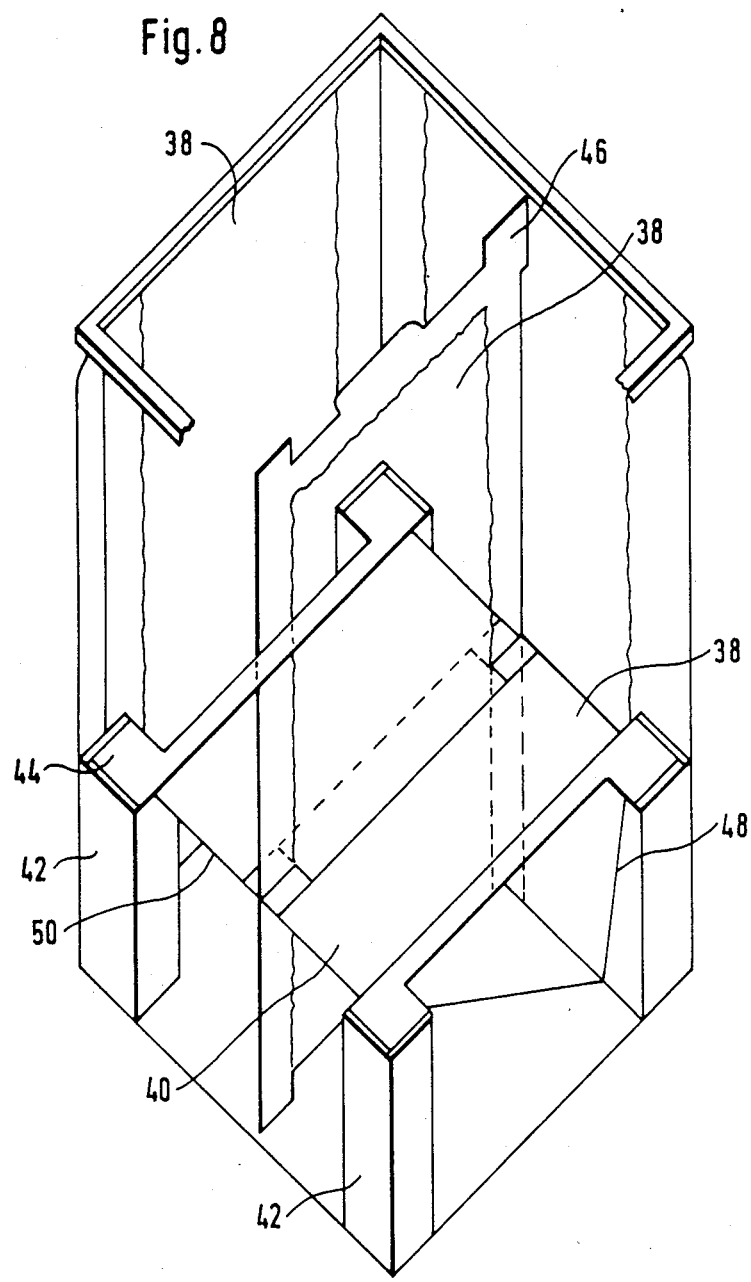
FIG. 8 is a diagrammatic view of the kit of FIG. 1.

As shown in FIGS. 7 and 8, bottom 40 can comprise, on each side of partition 46, feet 48 and 50. Each of feet 48 and 50 preferable consists of a rigid strip folded to define an elbow and to form, with the corresponding part of bottom 40, a triangular structure. Porous lining 38 of removable bottom 40 can extend over the entire surface of each of feet 48 and 50.

The triangular structure of each of feet 48 and 50 is preferably irregular or asymmetrical. This makes it possible to orient feet 48 and 50 in the opposite direction one to the other in order to form, viewed perpendicular to the partition 46 as in FIG. 7, a structure in the form of a "W". This allows the basket, consisting of partition 46, bottom 40 and its feet 48 and 50, when detached from container 10 (for example for the purposes of cleaning container 10 or for facilitating the removal of the prostheses) to be placed on a horizontal surface with, as the only bearing, the sharp edges of feet 48 and 50.

The upper part of middle partition 46 can comprise a flap which holds partition 46 in place and is not provided with porous lining 38.

Container 10 shown in FIGS. 5 to 8 is suitable for the simultaneous sterilization, storage and transport of dental prostheses. The prostheses being at all times maintained outside the reserve of sterilizing liquid by virtue of removable bottom 40, but at all times being in an atmosphere saturated with sterilizing vapors by virtue of the multiple evaporation surfaces constituted by porous linings 38. However, it is also possible to use container 10 for sterilization by immersion. For this purpose the inside basket, consisting of partition 46 and bottom 40 is removed in order to immerse the prosthesis or prostheses in the reserve of sterilizing liquid.

Figure 9:
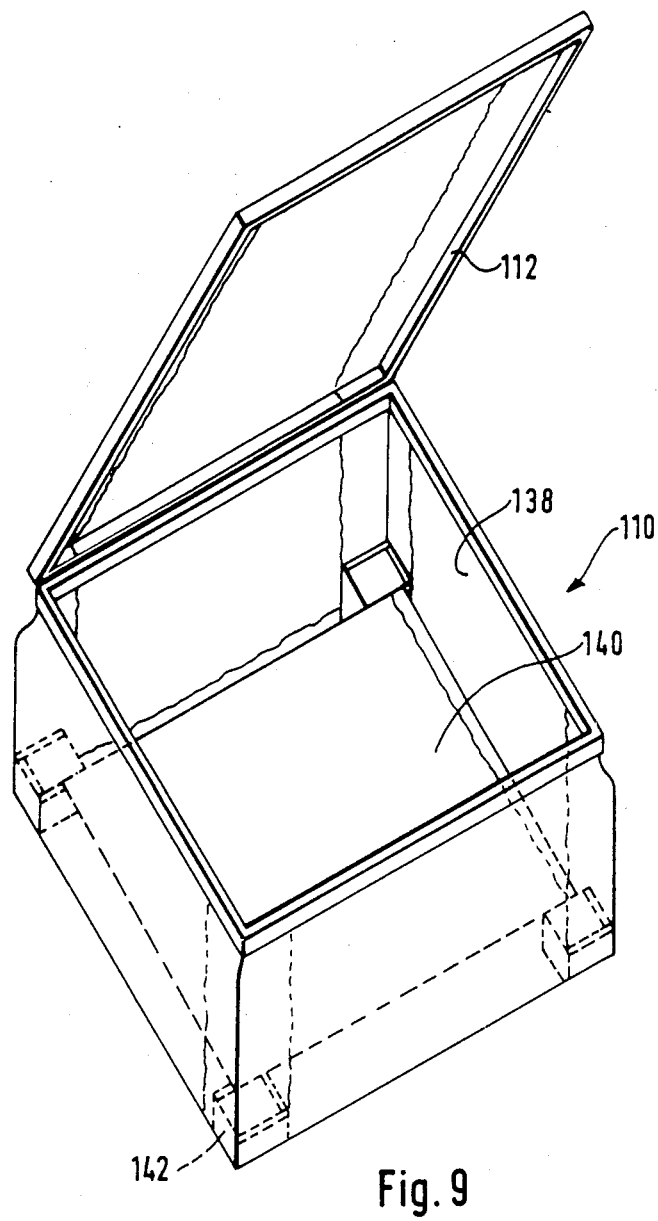
FIG. 9 is a front perspective view of an alternate embodiment of the kit of FIG. 1.

FIG. 9 shows a simplified version of the embodiment described above with reference to the preceeding figures. A container 110 in FIG. 9 is a smaller container than container 10 and can be used both as a case "by immersion", if it is filled completely, and also "by capillarity", if only the small false bottom is filled. The case comprises a swinging lid 112 with hermetic sealing, a removable false bottom 140 which rests freely on small blocks 142, as in the previous embodiment, and which comprises a tongue (not shown) which makes it possible to easily remove removable bottom 140 for the purposes of cleaning. Both the lateral faces and the lid and false bottom are equipped with a porous lining 138 in order to stimulate the evaporation of the sterilizing liquid.

It will be appreciated that the present invention applies equally to removable orthodontic apparatuses and, in a general manner, to all removable dental apparatuses.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A kit for the hygiene of removable dental prostheses comprising:
 a container with hermetic sealing which can contain at least one prosthesis, said container including an inner surface, said container being adapted to contain a sterilizing liquid;
 a removable false bottom in said container, said false bottom being adapted to support the prosthesis above a level of a solution of sterilizing liquid;
 and a porous lining covering at least a portion of said inner surface of said container and said false bottom.

2. The kit of claim 1 wherein:
 said container has the form of an upright parallelepiped of rectangular cross-section including lower corners;
 and said removable false bottom rests on four blocks provided, respectively, in each of said lower corners of said container.

3. The kit of claim 2 wherein:
 said corners of said removable bottom are each configured as a square projection relative to adjacent sides in order to bear on said blocks.

4. The kit of claim 1 wherein:
 said container is divided into two adjacent compartments, by a removable middle partition.

5. The kit of claim 4 wherein:
 said middle partition and said removable bottom are detachably connected in order to form a removable basket.

6. The kit of claim 5 wherein:
 said removable bottom comprises, on each side of said middle partition and on the lower side a foot, said foot comprising a strip folded in the form of a "V" and forming, together with said removable bottom, a triangular structure, each foot being provided with a porous lining.

7. The kit of claim 6 wherein:
 said triangular forms of said feet are asymmetrical so as to present in combination, viewed perpendicular to said middle partition, the form of a "W".

8. The kit of claim 1 wherein:
 said wall of said container comprises, at the level of said false bottom, a transparent section for checking the liquid level.

9. The kit of claim 1 wherein:
 said container comprises, on two opposite side faces, two opposite depressions for gripping.

10. The kit of claim 1 further including:
 a prosthesis-cleaning brush including a rectilinear sleeve, one of the ends of which terminates in a brush of conical form with the opposite end terminating in a brush having the form of a semiparaboloid.

11. The kit of claim 10 wherein:
 said end comprising said conical brush is inclined relative to said rectilinear sleeve.

12. The kit of claim 10 wherein:
 said rectilinear sleeve comprises two rims delimiting a section for attachment between two flexible tongues provided on one of the external side faces of said container.

13. The kit of claim 1 wherein:
 said hermetic sealing of said container is achieved by a swinging lid comprising a two-stage closure system.

* * * * *